United States Patent [19]
Zilch et al.

[11] Patent Number: 6,080,734
[45] Date of Patent: Jun. 27, 2000

[54] LIPONUCLEOTIDES OF SECO-NUCLEOSIDES, THEIR PRODUCTION AS WELL AS THEIR USE AS ANTIVIRAL PHARMACEUTICAL AGENTS

[75] Inventors: Harald Zilch, Mannheim; Dieter Herrmann, Heidelberg, both of Germany

[73] Assignee: Roche Diagnostic GmbH, Mannheim, Germany

[21] Appl. No.: 09/209,484

[22] Filed: Dec. 11, 1998

Related U.S. Application Data

[63] Continuation of application No. 08/869,737, Jun. 5, 1997, abandoned, which is a continuation of application No. 08/379,436, Feb. 8, 1995, abandoned.

[30] Foreign Application Priority Data

Aug. 8, 1992 [DE] Germany ............................ 42 26 279

[51] Int. Cl.⁷ ........................ A61K 31/675; C07F 9/6561
[52] U.S. Cl. ............................................... 514/81; 544/244
[58] Field of Search .................................. 544/244; 514/81

[56] References Cited

FOREIGN PATENT DOCUMENTS

| 350287 | 1/1990 | European Pat. Off. . |
| 92/03462 | 3/1992 | WIPO . |

OTHER PUBLICATIONS

Welch et al, *Acta Chemica. Scandinavica* B39, p 47–54, 1985.

*Primary Examiner*—Emily Bernhardt
*Attorney, Agent, or Firm*—Arent Fox Kintner Plotkin + Kahn

[57] ABSTRACT

The present invention is directed to new phospholipid derivatives of acyclovir and ganciclovir that link a lipid moiety, which represents a substituted C3 backbone, to acyclovir or ganciclovir via phosphate or thiophosphate. The compounds are particularly suitable for the therapy of viral infections.

11 Claims, No Drawings

LIPONUCLEOTIDES OF SECO-NUCLEOSIDES, THEIR PRODUCTION AS WELL AS THEIR USE AS ANTIVIRAL PHARMACEUTICAL AGENTS

This application is a continuation of application Ser. No. 08/869,737, filed Jun. 5, 1997 now abandoned, which is a continuation of application Ser. No. 08/379,436, filed Feb. 8, 1995 now abandoned.

The present invention concerns new phospholipid derivatives of seco-nucleosides that link a lipid moiety which represents a substituted C3 backbone with a seco-nucleoside via a phosphate or thiophosphate as well as their use as antiviral pharmaceutical agents.

The invention concerns compounds of formula I,

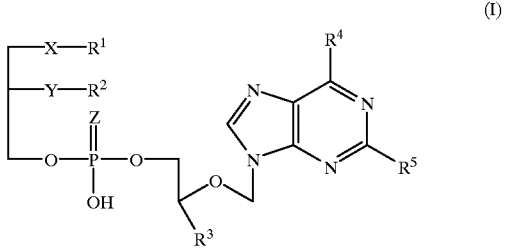

in which
$R^1$ denotes a straight-chained or branched, saturated or unsaturated aliphatic residue with 1–20 carbon atoms which can be substituted, if desired, once or several times by phenyl, halogen, $C_1$–$C_6$ alkoxy, $C_1$–$C_6$ alkylmercapto, $C_1$–$C_6$ alkoxycarbonyl, $C_1$–$C_6$ alkylsulfinyl or $C_1$–$C_6$ alkylsulfonyl groups, $R^2$ denotes a straight-chained or branched, saturated or unsaturated aliphatic residue with 1–20 carbon atoms which can be substituted, if desired, once or several times by phenyl, halogen, $C_1$–$C_6$ alkoxy, $C_1$–$C_6$ alkylmercapto, $C_1$–$C_6$ alkoxycarbonyl, $C_1$–$C_6$ alkylsulfinyl or $C_1$–$C_6$ alkylsulfonyl groups, $R^3$ denotes hydrogen or a $C_1$–$C_6$ alkyl group which is substituted, if desired, by hydroxy $R^4$ can be hydrogen, hydroxy, amino or an amino group substituted once or twice by $C_1$–$C_6$ alkyl, $R^5$ can be hydrogen, hydroxy, amino or an amino group substituted once or twice by $C_1$–$C_6$ alkyl, X represents a valency dash, oxygen, sulphur, sulfinyl or sulfonyl, Y can have the same meaning as X and the two groups X and Y can be the same or different, Z can be oxygen or sulphur, their tautomers and their physiologically tolerated salts of inorganic and organic acids and bases.

Since the compounds of the general formula I contain asymmetric carbon atoms, all optically active forms and racemic mixtures of these compounds are also the subject matter of the present invention.

The production and use of liponucleotides as antiviral pharmaceutical agents are described in J. Biol. Chem. 265, 6112 (1990) and EP 0 350 287. In this case only dimyristoylphosphatidyl and dipalmitoylphosphatidyl residues with their fatty acid ester structure coupled to known nucleosides such as e.g. AZT (azidothymidine) and ddC (dideoxycytidine) were examined and synthesized. EP 0 350 287 describes the respective 1,2-diesters of glycerol.

In J. Med. Chem. 33, 1380 (1990) nucleoside conjugates of thioether lipids with cytidine diphosphate are described which exhibit an antitumour action and which can be used in oncology.

5'-(3-SN-phosphatidyl)nucleosides having an antileukaemic activity are described in Chem. Pharm. Bull. 36, 209 (1988), as well as their enzymatic synthesis from the appropriate nucleosides and phosphocholines in the presence of phospholipase D having transferase activity.

Liponucleotides with a cyclic sugar moiety in the nucleoside which have an antiviral action are described in the patent application PCT/EP91/01541.

The Acyclovir-phospholipid conjugate from L-α-dimyristoylphosphatidyl acid and Acyclovir is described in Acta Chem. Scand., Ser. B. 39, 47 (1985) [cf. also organophosphorus Chem. 18, 187 (1987)].

The ether-/thioether lipids (X, Y=O or S) of the present invention are novel and also exhibit valuable pharmacological properties. They are particularly suitable for the therapy and prophylaxis of infections which are caused by DNA viruses such as e.g. the herpes-simplex virus, the cytomegaly virus, papilloma viruses, the varicella-zoster virus or Epstein-Barr virus or RNA viruses such as toga viruses or retroviruses such as the oncoviruses HTLV-I and II as well as the lentiviruses Visna and human immunodeficiency virus HIV-1 and 2.

The compounds of formula I appear to be particularly suitable for treating clinical manifestations of viral herpes infection in humans. The compounds of the general formula I act antivirally without being cytotoxic in pharmacologically relevant doses.

The compounds are additionally distinguished by a very good oral tolerance with good bioavailability.

The compounds of the present invention and their pharmaceutical preparations can also be used in combination with other pharmaceutical agents for the treatment and prophylaxis of the above-mentioned infections. Examples of these agents containing further pharmaceutical agents which can be used for the treatment and prophylaxis of HIV infections or diseases which accompany this illness are 3'-azido-3'-deoxy-thymidine (AZT), 2',3'-dideoxynucleosides such as e.g. 2'-3-dideoxycytidine (ddC), 2',3'-dideoxyadenosine and 2',3'-dideoxyinosine (ddI) or non-nucleosidic RT inhibitors such as HEPT, Nevirapin or L-697, 661 and corresponding derivatives. The compounds of the present invention and the other pharmaceutical agent can each be administered individually, simultaneously and optionally in a single or two separate formulations or at different times.

Alkali, alkaline-earth and ammonium salts of the phosphate group come into consideration as possible salts of compounds of the general formula I. Lithium, sodium and potassium salts are preferred as alkali salts. In particular magnesium and calcium salts come into consideration as the alkaline-earth salts. According to the invention ammonium salts are understood as salts which contain the ammonium ion which can be substituted up to four times by alkyl residues with 1–4 carbon atoms and/or aralkyl residues, preferably benzyl residues. The substituents can in this case be the same or different.

The compounds of the general formula I can contain basic groups, in particular amino groups, which can be converted into acid addition salts using suitable organic and inorganic acids. Hydrochloric acid, hydrobromic acid, sulphuric acid, phosphoric acid, fumaric acid, succinic acid, tartaric acid, citric acid, lactic acid, maleic acid or methanesulfonic acid come for example into consideration as the acid.

In the general formula I $R^1$ preferably denotes a straight-chained $C_9$–$C_{14}$ alkyl group which can additionally be substituted by a $C_1$–$C_6$ alkoxy or a $C_1$–$C_6$ alkylmercapto group. $R^1$ in particular represents a decyl, undecyl, dodecyl, tridecyl or tetradecyl group. Methoxy, ethoxy, butoxy and hexyloxy groups preferably come into consideration as the $C_1$–$C_6$ alkoxy substituents of $R^1$. If $R^1$ is substituted by a $C_1$–$C_6$ alkylmercapto residue, this is to be understood in particular as a methylmercapto, ethylmercapto, propylmercapto, butylmercapto and hexylmercapto residue.

$R^2$ preferably denotes a straight-chained $C_9$–$C_{14}$ alkyl group which can in addition be substituted by a $C_1$–$C_6$ alkoxy group or a $C_1$–$C_6$ alkylmercapto group. $R^2$ in particular represents a decyl, undecyl, dodecyl, tridecyl or tetradecyl group. The methoxy, ethoxy, propoxy, butoxy and hexyloxy group preferably come into consideration as the $C_1$–$C_6$ alkoxy substituents of $R^2$. If $R^2$ is substituted by a $C_1$–$C_6$ alkylmercapto residue, then this is understood in particular to be a methylmercapto, ethylmercapto, butylmercapto and hexylmercapto residue.

In the definition of $R^3$ the alkyl group denotes in particular a straight-chained or branched alkyl group preferably having up to four C atoms such as e.g. methyl, ethyl, n-propyl, isopropyl or n-butyl. These alkyl groups are preferably substituted by one or two hydroxy groups such as e.g. hydroxymethyl, 2-hydroxyethyl or 3-hydroxypropyl.

$C_1$–$C_6$ alkyl groups in general denote straight-chained or branched alkyl residues preferably having up to four C atoms such as e.g. methyl, ethyl, n-propyl, isopropyl, n-butyl or isobutyl.

$R^4$ preferably denotes a hydroxy or amino group.

$R^5$ in particular denotes hydrogen or a hydroxy or amino group.

X and Y preferably represent an oxygen or sulphur atom. Z is preferably an oxygen atom.

Especially preferred coupled seco-nucleosides in the claimed liponucleotides of the general formula I are Ganciclovir or Acyclovir.

The compounds of formula I can be prepared by reacting
1. a compound of formula II,

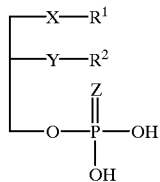

(II)

in which $R^1$, $R^2$, X, Y and Z have the stated meanings, with a compound of the general formula III,

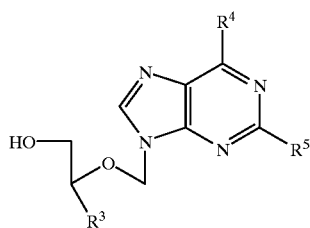

(III)

in which $R^3$, $R^4$ and $R^5$ have the above-mentioned meaning using a condensing agent such as DCC (dicyclohexylcarbodiimde) in pyridine or in the presence of 2,4,6-triisopropylbenzenesulfonic acid chloride and a tert. nitrogen base e.g. pyridine or lutidine in an inert solvent such as e.g. toluene or directly in pyridine and, after hydrolysis is completed, the oxygen protecting groups are cleaved if desired according to conventional methods in nucleoside chemistry or 2. a compound of formula IV

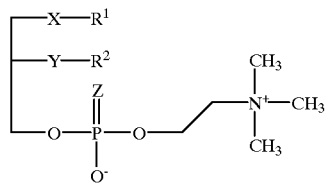

(IV)

in which $R^1$, $R^2$, X, Y and Z have the above-mentioned meaning is reacted with a compound of formula III in which $R^3$, $R^4$ and $R^5$ have the stated meanings in the presence of phospholipase D in an inert solvent such as e.g. chloroform in the presence of a buffer and, after the reaction is completed, the oxygen protecting group is cleaved if desired according to conventional methods in nucleoside chemistry.

The production of compounds of formula II and IV is described in DE 39 29 217.7 and WO 91/05558.

The production of compounds of the general formula III is described in Progress in Medicinal Chemistry, vol. 23, 187 (1986) and in the literature cited there.

Acyclovir and Ganciclovir are commercially available.

The pharmaceutical agents containing compounds of formula I for the treatment of viral infections can be administered enterally or parenterally in a liquid or solid form. The usual methods of administration come into consideration in this case such as for example tablets, capsules, coated tablets, syrups, solutions or suspensions. Water is preferably used as the injection medium which contains the usual additives for injection solutions such as stabilizers, solubilizers and buffers. Such additives are e.g. tartrate and citrate buffer, ethanol, complexing agents such as ethylenediaminetetraacetic acid and their non-toxic salts, high molecular polymers such as liquid polyethylene oxide to regulate viscosity. Liquid carrier materials for injection solutions have to be sterile and are preferably dispensed into ampoules. Solid carrier materials are for example starch, lactose, mannitol, methylcellulose, talcum, highly dispersed silicic acid, higher molecular fatty acids such as stearic acid, gelatin, agar-agar, calcium phosphate, magnesium stearate, animal and plant fats, solid high molecular polymers such as polyethylene glycols etc. Suitable preparations for oral applications can if desired contain flavourings or sweeteners.

The dosage can depend on various factors such as mode of administration, species, age or individual condition. The compounds according to the invention are usually administered in amounts of 0.1–100 mg, preferably 0.2–80 mg per day and per kg body weight. It is preferable to divide the daily dose into 2–5 administrations, 1–2 tablets being administered at each application with a content of active substance of 0.5–500 mg. The tablets can also be retarded by which means the number of applications per day can be reduced to 1–3. The content of active substance of the retarded tablets can be 2–1000 mg. The active substance can also be administered by continuous infusion in which case amounts of 5–1000 mg per day are normally sufficient.

The following compounds of formula I come into consideration within the sense of the present invention in addition to the compounds mentioned in the examples and combinations of all the meanings mentioned in the claims for the substituents:

1. 2'-[9-(ethoxymethyl)guanine]phosphoric acid-(3-dodecylmercapto-2-decyloxy)-1-propyl ester
2. 2'-(9-{[(1-hydroxymethyl)ethoxy]methyl}guanine) phosphoric acid-(3-dodecylsulfonyl-2-decyloxy)-1-propyl ester
3. 2'-(9-{[(1-hydroxymethyl)ethoxy]methyl}guanine) phosphoric acid-(3-dodecylsulfonyl-2-decyloxy)-1-propyl ester
4. 2'-(9-{[(1-hydroxymethyl)ethoxy]methyl}guanine) phosphoric acid-(3-dodecylmercapto-2-decyloxy)-1-propyl ester
5. 2'-[9-(ethoxymethyl)guanine]phosphoric acid-(3-undecylmercapto-2-decyloxy)-1-propyl ester
6. 2'-[9-(ethoxymethyl)guanine]phosphoric acid-(3-dodecyloxy-2-decyloxy)-1-propyl ester
7. 2'-(9-{[(1-hydroxymethyl)ethoxy]methyl}guanine) phosphoric acid-(3-dodecylmercapto-2-nonyloxy)-1-propyl ester
8. 2'-(9-{[(1-hydroxymethyl)ethoxy]methyl}guanine) phosphoric acid-(3-dodecylmercapto-2-decylmercapto)-1-propyl ester
9. 2'-(9-{[(1-hydroxymethyl)ethoxy]methyl}guanine) phosphoric acid-(3-undecylmercapto-2-decyloxy)-1-propyl ester
10. 2'-[9-(ethoxymethyl)guanine]phosphoric acid-(3-tridecylmercapto-2-decyloxy)-1-propyl ester
11. 2'-(9-{[(1-hydroxymethyl)ethoxy]methyl}guanine) phosphoric acid-(3-tridecylmercapto-2-decyloxy)-1-propyl ester
12. 2'-[9-(ethoxymethyl)guanine]phosphoric acid-(3-dodecylmercapto-2-dodecyloxy)-1-propyl ester
13. 2'-[9-(ethoxymethyl)guanine]phosphoric acid-(3-dodecylmercapto-2-undecyloxy)-1-propyl ester
14. 2'-(9-{[(1-hydroxymethyl)ethoxy]methyl}guanine) phosphoric acid-(2,3-bis(dodecylmercapto)-1-propyl ester
15. 2'-(9-{[(1-hydroxymethyl)ethoxy]methyl}guanine) phosphoric acid-(3-dodecylmercapto-2-dodecyloxy)-1-propyl ester
16. 2'-[9-(ethoxymethyl)guanine]phosphoric acid-(3-undecyloxy-2-dodecyloxy)-1-propyl ester
17. 2'-[9-(ethoxymethyl)guanine]phosphoric acid-(3-decylsulfonyl-2-dodecyloxy)-1-propyl ester
18. 2'-[9-(ethoxymethyl)guanine]phosphoric acid-(3-decyloxy-2-decyloxy)-1-propyl ester
19. 2'-[9-(ethoxymethyl)guanine]phosphoric acid-(3-dodecylmercapto-2-dodecyloxy)-1-propyl ester
20. 2'-(9-{[(1-hydroxymethyl)ethoxy]methyl}guanine) phosphoric acid-(3-tetradecylmercapto-2-decyloxy)-1-propyl ester
21. 2'-[9-(ethoxymethyl)guanine]phosphoric acid-(3-pentadecylmercapto-2-decyloxy)-1-propyl ester
22. 2'-(9-{[(1-hydroxymethyl)ethoxy]methyl}guanine) phosphoric acid-(3-tridecylmercapto-2-decyloxy)-1-propyl ester
23. 2'-[9-(ethoxymethyl)guanine]phosphoric acid-(3-dodecylmercapto-2-octyloxy)-1-propyl ester

EXAMPLE 1

Phosphoric acid-(3-dodecylmercapto-2-decyloxy)-1-propyl ester

A suspension of 4.26 g $P_4O_{10}$ in 60 ml absolute pyridine was admixed at room temperature with 13 ml hexamethyldisiloxane and heated to 100° C. for 1 hour. It was then slightly cooled, admixed with 25 g 3-dodecylmercapto-2-decyloxy-1-propanol and heated for a further 2.5 hours to 100° C.

After completely cooling to room temperature and removing the highly volatile components in a vacuum, the phosphate could be extracted with ether from the aqueous suspension of the residue. The evaporation residue of the ether phase was purified by column chromatography on silica gel 60 or RP 18. Yield 18.7 g (63%), $R_f$=0.66 ($CH_2Cl_2$/ MeOH/$H_2O$ 6.5/2.5/0.4) on TLC plates, Merck 5715, silica gel 60.

EXAMPLE 2

2'-(9-{[(1-hydroxymethyl)ethoxy]methyl}guanine) phosphoric acid-(3-dodecylmercapto-2-decyloxy)-1-propyl ester 1.45 g (3 mmol) phosphoric acid-(3-dodecylmercapto-2-decyloxy)-1-propyl ester and 770 mg (3 mmol) Ganciclovir were twice admixed with 20 ml absolute pyridine each time and evaporated. The residue was taken up in 20 ml absolute pyridine, 2.7 g (8.5 mmol) 2,4,6-triisopropylbenzenesulfonic acid chloride was added under nitrogen and it was stirred for 24 hours at 40° C. Then 10 ml water was added, the mixture was stirred for a further 2 hours at room temperature and the solvent was removed in a rotary evaporator.

The oily residue was freed from residual pyridine by evaporation with toluene and purified by means of column chromatography on RP 1.8 with a linear gradient of methanol/water 7/3 to 9.5/0.5 as the eluant. Yield 0.75 g (34% of theory), oil. $R_f$=0.73 ($H_2O$/MeOH 0.5/9.5) on RP 8, $R_f$=0.30 ($CH_2Cl_2$/MeOH/$H_2O$ 6.5/2.5/0.4) on TLC plates, Merck 5715, silica gel 60 F.

EXAMPLE 3

2'-[9-(ethoxymethyl)guanine]phosphoric acid-(3-dodecylmercapto-2-decyloxy)-1-propyl ester This compound was produced analogously to example 1 from Acyclovir in a 47% yield, oil, $R_f$=0.77 ($H_2O$/MeOH 0.5/9.5) on RP 8, $R_f$=0.35 ($CH_2Cl_2$/MeOH/$H_2O$ 6.5/2.5/0.4) on TLC plates, Merck 5715, silica gel 60.

What is claimed is:

1. A liponucleotide of the formula I

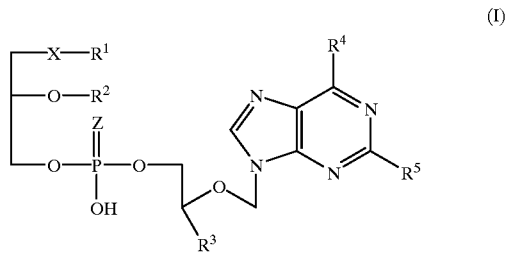

wherein $R^1$ and $R^2$ are each independently a straight-chained or branched, saturated or unsaturated $C_1$–$C_{20}$ alkyl group which is unsubstituted or substituted at least once by phenyl, halogen, $C_1$–$C_6$ alkoxy, $C_1$–$C_6$ alkylmercapto, $C_1$–$C_6$ alkoxycarbonyl, $C_1$–$C_6$ alkylsulfinyl or $C_1$–$C_6$ alkylsulfonyl;

$R^3$ is hydrogen or $CH_2OH$;

$R^4$ is hydroxy;

$R^5$ is amino;

X is sulfur, sulfinyl or sulfonyl; and

Z is oxygen or sulfur, or a tautomer thereof, or a physiologically tolerated salt thereof with an inorganic or organic acid or base.

2. The liponucleotide of claim 1, wherein $R^1$ is a straight-chained $C_9$–$C_{14}$ alkyl group which is unsubstituted or substituted by $C_1$–$C_6$ alkoxy or $C_1$–$C_6$ alkylmercapto.

3. The liponucleotide of claim 1, wherein $R^1$ is a decyl, undecyl, dodecyl, tridecyl or tetradecyl group, which group is unsubstituted or is substituted by a methoxy, ethoxy, butoxy, hexyloxy, methylmercapto, ethylmercapto, propylmercapto, butylmercapto or hexylmercapto group.

4. The liponucleotide of claim 1, wherein $R^2$ is a straight-chained $C_9$–$C_{14}$ alkyl group which is unsubstituted or substituted by $C_1$–$C_6$ alkoxy or $C_1$–$C_6$ alkylmercapto.

5. The liponucleotide of claim 1, wherein $R^1$ is a decyl, undecyl, dodecyl, tridecyl or tetradecyl group, which group is unsubstituted or is substituted by a methoxy, ethoxy, butoxy, hexyloxy, methylmercapto, ethylmercapto, butylmercapto or hexylmercapto group.

6. The liponucleotide of claim 1, wherein X is sulfur.

7. The liponucleotide of claim 1, wherein Z is oxygen.

8. The liponucleotide of claim 1, wherein $R^3$ is hydrogen.

9. The liponucleotide of claim 1, wherein $R^3$ is $CH_2OH$.

10. A method of treating a viral herpes infection in a patient in need thereof, comprising administering to the patient an antiviral effective amount of a liponucleotide according to claim 1.

11. A pharmaceutical composition, comprising a liponucleotide according to claim 1 and a pharmaceutically acceptable carrier.

* * * * *